Figure 1:
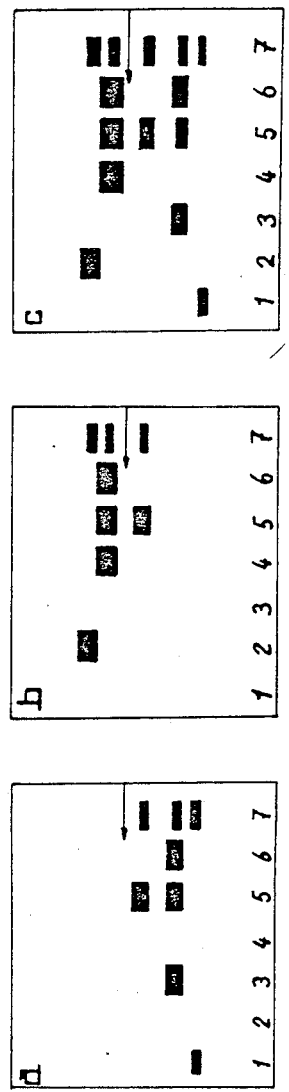

United States Patent [19]

Lansdorp

[11] Patent Number: 4,868,109

[45] Date of Patent: Sep. 19, 1989

[54] IMMUNOLOGICAL ANTIBODY COMPLEX, ITS PREPARATION AND ITS USE

[76] Inventor: Peter M. Lansdorp, 3431 W. 24th Ave., Vancouver, B.C. V6S 1L3, Canada

[21] Appl. No.: 855,688

[22] Filed: Apr. 25, 1986

[30] Foreign Application Priority Data

Apr. 29, 1985 [NL] Netherlands .......................... 8501219

[51] Int. Cl.[4] ..................... C12Q 1/28; A61K 39/295
[52] U.S. Cl. ..................................... 435/28; 424/85.8; 424/86; 424/85.91; 435/7; 436/518; 436/519; 436/520; 436/536; 436/547; 530/387; 530/388; 530/389; 530/402; 530/403
[58] Field of Search ....................... 530/387, 388, 389; 424/85, 86; 436/512, 513; 435/7, 28

[56] References Cited

U.S. PATENT DOCUMENTS

| | | | |
|---|---|---|---|
| 4,355,023 | 10/1982 | Ehrlich et al. | 530/388 |
| 4,470,925 | 9/1984 | Auditore-Hargreaves | 530/388 |
| 4,481,298 | 11/1984 | Cone et al. | 530/387 |
| 4,578,360 | 3/1986 | Smith | 530/387 |
| 4,676,980 | 6/1987 | Segal et al. | 530/387 |

FOREIGN PATENT DOCUMENTS

| | | |
|---|---|---|
| 0081949 | 6/1983 | European Pat. Off. . |
| 0096463 | 12/1983 | European Pat. Off. . |
| WO83/03679 | 10/1983 | World Int. Prop. O. . |

OTHER PUBLICATIONS

Lansdorp et al.—Chem. Abst. vol. 105 (1986) p. 40810g.
Chemical Abstracts, vol. 73, Nr. 5, Aug. 3, 1970 p. 75, Abstract Nr. 22071h, Columbus, Ohio, U.S.; L. A. Sternberger et al. "Unlabelled Antibody Enzyme Method of Immunohistochemistry, Preparation and Properties of Soluble Antigen—Antibody Complex (Horseradish Peroxidase —Anti—Horseradish Peroxidase) and its Use in Identification of Sprirochetes".
J. Histochem. Cytochem., vol. -18, No. 5, 1970, pp. 315–333.
Boorsma, "Preparation of HRP—labelled Antibodies" in Immunohistochemistry 20 (1983), pp. 87–100.
Milstein and Cuello, "Hybrid Hybridomas and Their Use in Immunohistochemistry" in Nature V. 305 No. 6 (1983), pp. 538–540.

Primary Examiner—Sam Rosen
Attorney, Agent, or Firm—Rogers, Bereskin & Parr

[57] ABSTRACT

The invention relates to an immunological complex of two antibodies of a first animal species, e.g. mouse antibodies, which have been conjugated to form a cyclic tetramer with two monoclonal antibodies of a second animal species, e.g. rat monoclonal antibodies, directed against the Fc-fragment of the antibodies of the first animal species.

Preferably, the complex is bifunctional, that is to say, that it contains two different antibodies of the first animal species, one of which is preferably directed to a detectable substance, such as an enzyme, e.g. peroxidase, and the other is directed to any desired antigen. A tetrameric complex of this kind may be used as a labelled antibody in immunoassays.

Further, the invention relates to processes for preparing the complexes and for using the complexes in immunological reactions. Finally, the invention relates to drugs containing a complex according to the invention, as the complexes may be used to direct certain active principles to target cells.

34 Claims, 2 Drawing Sheets

IMMUNOLOGICAL ANTIBODY COMPLEX, ITS PREPARATION AND ITS USE

When carrying out immunological determinations, measurement of the extent to which an immunological reaction (antigen-antibody reaction) has proceeded, is necessary. Generally, the antigen or the antibody therefore has to be provided with a detectable group (label). For this purpose various methods are in use already, of which labelling with radioactive, fluorescent, chemiluminescent or enzymatically active atoms or groups may be mentioned. Generally, these detectable groups or atoms are introduced into the antigen or into the antibody by chemical means. Various chemical coupling methods, especially for enzymes, are discussed in Immunohistochemistry 20 (1983), pages 87-100. In chemical coupling of enzymes to antibodies bifunctional coupling agents reacting with the enzyme and with the antibody are generally used. The chemical coupling methods have various disadvantages. Thus, the antibody may be denatured by reaction with the coupling agent, and enzyme coupled with itself, as well as antibody coupled with itself are always obtained together with the desired labelled antibody.

Another approach to the labelling of antibodies is described in Nature 305 (1983), pages 537-540. This publication relates to the production of hybrid antibodies which are capable of binding with two different antigens. The production of these hybrid antibodies is effected by means of hybrid hybridomas. Especially, an anti-somatostatine-anti-peroxidase antibody is described which, consequently, is capable of reacting with a label, the enzyme peroxidase, as well as with somatostatine. Although these bifunctional antibodies constitute an improvement with respect to the chemically labelled antibodies, they still have the disadvantage that a hybridoma has to be constructed for each separate bifunctional antigen, which is highly time-consuming.

It was now found that immunological reagents possessing two different functions may be prepared in a much simpler way. Namely, it was found that antibodies of a first animal species form a cyclic tetrameric complex with monoclonal antibodies of a second animal species the Fab-fragments of which are directed against the Fc-fragments of the first animal species. The cyclic tetrameric complex is built from two molecules of antibodies of the first animal species and two molecules of the antibodies of the second animal species. These cyclic tetrameric complexes possess high stability. When the antibodies of the first animal species are different from each other the immunological complex is bifunctional and may be used in the same way as the above-mentioned bifunctional antibodies which may be produced with hybridomas.

In the first place the invention relates to an immunological complex built from two antibodies of a first animal species, which are conjugated to form a cyclic tetramer with two monoclonal antibodies of a second animal species directed against the Fc-fragment of the antibodies of the first animal species.

The most important embodiment of the invention is an immunological complex which is bifunctional and in which two different antibodies of the first animal species are conjugated to form a cyclic tetramer with two monoclonal antibodies of a second animal species directed against the Fc-fragment of the antibodies of the first animal species.

The formation of the cyclic tetrameric complexes according to the invention has been shown by means of electrophoresis on agar plates and by means of electron microscopy.

Thus, mouse antibodies of the immunoglobulin gamma-1 (IgG1) subclass against the enzyme peroxidase were mixed with a monoclonal rat antibody specific to mouse IgG1. Last-mentioned antibody was selected for its capability to bind two different mouse antibodies. On reaction of the anti-enzyme antibody with an equimolar amount of the rat antibody practically all of the enzyme binding activity appeared to migrate, in electrophoresis, as a single band with a mobility different from that of the separate antibodies. A similar test was carried out with mouse antibodies against the enzyme alkaline phosphatase. Also in this test a similar complex was formed.

The formation of the complexes proceeds extremely quickly, in any case within the time necessary to mix the antibodies, to apply a sample on the agar plate and to begin with the electrophoresis. The minimum time necessary for this is 20 seconds.

When the two anti-enzyme antibodies are first mixed with each other and then the monoclonal rat antibody is added three different complexes are formed, namely a complex containing exclusively the anti-peroxidase, a complex containing exclusively the anti-alkaline phosphatase and a complex containing both of the anti-enzyme antibodies. When the anti-enzyme antibodies are first mixed separately with the monoclonal rat antibody and then both of the so formed homologous complexes are mixed, a bifunctional complex is not formed. Apparently the complexes formed are so stable that no mutual exchange of antibodies takes place. When a lower than equivalent amount of the rat antibody is added to a mixture of the anti-enzyme antibodies the above-mentioned three complexes are also formed, but unbonded anti-enzyme antibody is left.

The structure of the complexes according to the invention was investigated with scanning transmission electron microscopy (STEM). In images of negatively stained complexes, structures could be observed which correspond to cyclic tetramers of immunoglobulins. Dominating in the image are tetrameric complexes of which the Fab-fragments of the mouse and rat antibodies together with the Fc-fragment of the rat antibodies are clearly visible. Certain details of the complexes, such as the domains and the two chains of the mouse-Fab-fragments, as well as the special orientation of the Fab- and Fc-fragments could be distinguished well.

Figure 2:
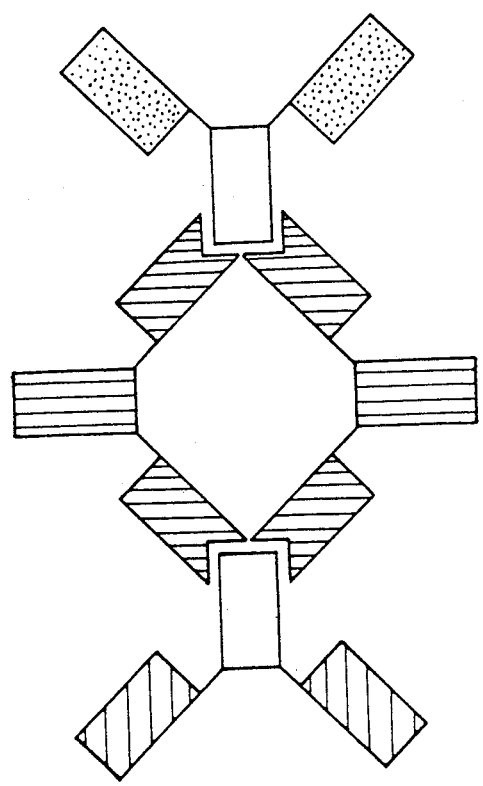

It appears clearly from the results of the agar-gelelectrophoresis which are illustrated in FIG. 1 and in example I, and from the electron microscopy that the cyclic tetrameric complexes are formed. The stable complexes according to the invention apparently have the structure as schematically indicated in FIG. 2.

When it is desired to prepare the bifunctional complexes, for example from antibodies against peroxidase, and from antibodies against a surface antigen on human blood platelets, both of the antibodies may be mixed in any desired ratio and the mixture may be reacted with the monoclonal antibody against the Fc-fragments of the two first mentioned antibodies. The highest yield of bifunctional complex is obtained, however, when the antibodies against peroxidase and the antibodies against a surface antigen on human blood platelets are mixed in equimolar ratio. As remarked above the reaction product always contains also homologous complexes, in the case of the example complexes containing only antibodies against peroxidase, and complexes containing only antibodies against the surface antigen on human blood platelets. These homologous complexes should not always interfere in the use of the reaction product as an immunological reagent. For example, when the above-mentioned reaction product is reacted with human blood platelets the complexes containing exclusively antibodies against peroxidase will not adhere to the blood platelets. The other complexes will do, but only the bifunctional complexes will give a reaction with platelets and a reaction with peroxidase.

If desired, the bifunctional complex may be isolated in pure condition, for example by means of anion exchange chromatography. Also, the ratio between the bifunctional complex and both of the homologous complexes in the reaction product can be influenced by changing the molar ratio of the antibodies of the first animal species used. Thus, when using the anti-peroxidase antibody and the antibody against a surface antigen on blood platelets in a higher ratio than 1:1, for example 5:1, a reaction product is obtained in which the ratio of the homologous complex containing exclusively anti-blood platelets antibodies, to the bifunctional complex is changed in favour of the bifunctional complex.

Among the bifunctional immunological complexes according to the invention those complexes are preferred in which the Fab-fragments of one of the antibodies of the first animal species are directed against a substance having a desired property, such as detectability, toxicity, therapeutical activity. In this connection it is a condition that such substances provoke the production of antibodies in an animal, including humans. Examples of detectable substances, which may provoke the production of antibodies are enzymes, such as horseradish peroxidase, alkaline phosphatase, glucose oxidase and galactosidase.

The other antibody which is formed into a bifunctional complex together with the antibody against a substance having a desired property, may be directed to any desired antigen. As examples of antigens against which the second antibody of the first animal species may be directed, there may be mentioned: surface membrane antigens, such as antigens on the surface of blood cells, for example erythrocytes or blood platelets, or viral antigens. Further, the second antibody of the first animal species can be directed to a specific antigen which is produced by a malignant cell. Bifunctional complexes containing such an antibody of the first animal species can be used not only for the detection of malignant cells, but also for directing substances which are toxic with respect to these cells towards the malignant cells. In the first case the first antibody of the first animal species is directed against a detectable substance, for example an enzyme, and in the second case against a substance inhibiting the growth of the malignant cells.

The animal species from which the antibodies of the present tetrameric complexes are derived, are not important. It is often convenient to combine mouse antibodies with rat antibodies. The monoclonal antibodies of the second animal species have to be directed against the Fc-fragments of the antibodies of the first animal species, and each of both of the Fab-fragments of the monoclonal antibodies of the second animal species have to be capable of binding with the Fc-fragment of one antibody of the first animal species.

The presence of an Fc-fragment in the monoclonal antibodies of the second animal species is not essential. In certain cases it may even be advantageous to split off the Fc-fragment from the antibodies of the second animal species before formation of the cyclic complex. This can be effected in a known way by means of an enzyme, for example pepsin.

Further, the invention relates to a bifunctional immunological complex as described above, which is coupled with the antigen against which one of the antibodies of the first animal species is directed. This antigen may be, for example, a detectable substance, such as an enzyme. In that case the complex has the properties of a labelled antibody. When the antigen is a substance having another desirable property, for example toxicity with respect to malignant cells, the complex can be used, for example, as a drug.

The invention also relates to a process for preparing immunological complexes, which is characterized in that antibodies of a first animal species are reacted with an about equivalent amount of antibodies of a second animal species which are directed against the Fc-fragments of the antibodies of the first animal species, and in that, if desired the tetrameric complex formed is isolated.

The preparation of a bifunctional complex coupled to an antigen, which also belongs to the invention, is effected by reaction of a bifunctional complex with the antigen in question.

Also, the invention relates to a process for carrying out immunological reactions, in which the bifunctional immunological complexes according to the invention are used. An example of such a reaction is the detection of human antibodies bonded to viral antigens which have been transferred to nitrocellulose paper after electrophoresis, by means of bispecific anti-human IgG/anti-alkaline phosphatase/alkaline phosphatase complexes.

The invention provides a simple, specific and efficient way to couple antibodies with each other and, for example, to label antibodies. Due to the high specificity of the monoclonal antibodies of the second animal species the use of non-purified antibodies is possible. The process for preparing tetrameric complexes is very simple and takes extremely little time. This is a large improvement in comparison with chemical labelling of antibodies. Also in comparison with the bifunctional monoclonal antibodies produced by hybrid cell lines the invention offers the advantage that it is not necessary to select cell lines, and that the complexes may be built from bivalent monoclonal antibodies having known properties.

The bifunctional complexes according to the invention may also be used for specific coupling of antigens. Suitable combinations of monoclonal antibodies may be used for identification and separation of antigens. Further, specific interactions which are induced by bifunctional or homologous tetrameric complexes may generally improve the effectivity of fusions, transfections and interactions between cells. Thus, for example, erythrocytes may be labelled with bifunctional complexes built from anti-erythrocyte antibodies and anti-HLA-DR antibodies. In this way bifunctional complexes may be used to direct or to improve interactions between cells. In this connection the use, in vivo, to direct certain effector cells to microorganisms, virus-infected cells and tumor cells, may be mentioned.

The homologous cyclic tetrameric complexes according to the invention may be used, for example, for detecting human antibodies on human red blood cells, for example Rhesus antibodies. In this case homologous complexes of anti-human IgG-antibodies are used as antiimmunoglobulin (Coomb's reagent) for the agglutination of sensitized erythrocytes.

The invention is illustrated in the following examples which, however, do not limit the invention in any way whatsoever.

EXAMPLE I

DETECTION OF THE FORMATION OF CYCLIC TETRAMERIC ANTIBODY COMPLEXES BY MEANS OF GEL ELECTROPHORESIS.

a. Mouse anti-peroxidase antibody.

Monoclonal mouse antibodies against horse-radish peroxidase* (CLB-HRP-1) were used for the gel electrophoresis. A stock solution (0.2 mg/ml, in phosphate buffered saline (PBS; pH 7.2)) of the antibody, which was purified over a protein-A-Sepharose column was diluted to the desired concentration with PBS.

b. Mouse anti-alkaline phosphatase antibody.

Monoclonal antibodies against alkaline peroxidase (CLB-AP-4) were used. Starting material was the 20×concentrated supernatant of the tissue culture containing 0.2 mg antibody/ml. This was diluted to the desired concentration with PBS.

*obvious error; phosphatase would be correct c. Monoclonal rat anti-mouse antibodies.

In the gel electrophoresis monoclonal rat antibodies against mouse IgG1 were used. These were obtained by fusion (Nature 266, 550–553 (1977)) of mouse-Sp2/0 Ag14 cells (Nature 274, 917–919 (1978)) with spleen cells of a Brown Norway rat which was immunized three times with various preparations of purified monoclonal mouse IgG1. The supernatants of the hybridoma cells were tested for the property to couple monoclonal mouse peroxidase-antiperoxidase (PAP) complexes to mouse IgG1 layered upon microtiter plates, by means of the ELISA technique. For further research a hybridoma cell line (CLB-Mδ1—1) was selected from a number of positively reacting cell lines, and was used for larger scale culturing. The IgG1-kappa-antibody produced by this cell line was purified by affinity chromatography on a mouse IgG1-Sepharose column.

d. Gel electrophoresis was carried out on agar plates according to Wieme "Gel Electroforesis" Elsevier Publ. Co., Amsterdam (1976).

The following products were introduced upon the lanes of three agar plates:

Lane 1: Monoclonal anti-peroxidase (anti-POD), 2.5 μl; 50 μg/ml.

Lane 2: Monoclonal anti-alkaline phosphatase (anti-AP), 2.5 μl; 50 μg/ml.

Lane 3: Anti-POD complexed with equal amount of monoclonal rat anti-mouse IgG1 (anti-mIgG1). Final concentration 50 μg/ml, calculated on anti-POD. 2.5 μl of the solution of the complex was introduced.

Lane 4: Anti-Ap complexed with equal amount of anti-IgG1. Final concentration 50 μg/ml, calculated on anti-AP. 2.5 μl of the solution of the complex was introduced.

Lane 5: Anti-POD, first mixed with an equal amount of anti-AP and then the mixture complexed with an amount of anti-mIgG1 equivalent with the total of the mouse antibodies. Final concentration 50 μg/ml calculated on the total of the mouse antibodies. 2.5 μl of the solution was introduced.

Lane 6: Complex of anti-POD with equal amount of anti-mIgG1 mixed with same amount of complex of anti-AP with anti-mIgG1. Final concentration 50 μg/ml calculated on the total of the mouse antibodies. 2.5 μl of the solution was introduced.

Lane 7: Anti-POD first mixed with an equal amount of anti-AP and the mixture then complexed with 40% of the amount of anti-mIgG1 equivalent with the total of anti-POD and anti-AP. Final concentration 50 μg/ml calculated on the total of the mouse antibodies. 2.5 μl of the solution was introduced.

The electrophoresis was carried out during 45 minutes at pH 8.5 and 300 volts. Then the agar plates were covered with nitrocellulose paper and filter paper and a pressure of about 0.1 kg/cm$^2$ was applied during 2 hours. The blots obtained were incubated in PBS, pH 7.2 with 3% (weight/volume) bovine serum albumin (BSA) during 16 hours.

The three blots so obtained were treated in different ways with enzymes, and developed. The results are shown in FIG. 1.

Blot a (FIG. 1) was incubated for 2 h with PBS-BSA containing peroxidase labelled human kappa-chains specific rabbit immunoglobulins (DAKO, Copenhagen, Denmark, codenumber p-129) in a dilution of 1:100. These labelled immunoglobulins gave a stronger colour reaction with the monoclonal anti-peroxidase antibody bonded to the nitrocellulose than purified (monovalent) peroxidase. The blots were washed three times during five minutes with PBS containing 0.1 percent by weight of Tween 20, and were incubated once during 20 minutes with 0.5 mg/ml diaminobenzidine (Sigma, Grade II) in 0.05M tris-buffer, pH 7.5 containing 0.01 percent by weight of H$_2$O$_2$. Then the result was photographed.

Blot b (FIG. 1) was incubated during 2 h with PBS-BSA containing alkaline phosphatase (Sigma, Grade VII, catalogue number p-5521) in a concentration of 10 μg/ml. The blots were washed three times during 5 minutes with PBS containing 0.1 percent by weight of Tween 20 and were incubated once during 20 minutes with 0.2 mg/ml naphthol-AS-MX-phosphate (Sigma) in 0.1M tris-buffer, pH 8.2 containing 1 mg/ml Fast Red TR (Sigma). Then the result was photographed.

Blot c (FIG. 1) was obtained by first carrying out the same steps as with blot a and, after the treatment with the peroxidase substrate, washing three times with PBS containing 0.1 percent Tween 20, then incubating with the alkaline phosphatase, washing again and then developing with the phosphatase substrate.

The results show that the mouse antibodies form a stable complex with the monoclonal rat-antimouse antibodies. Namely, in lane 6 of FIG. 1a and FIG. 1b one sees only one reaction product. In lane 6 of FIG. 1c two reaction products are shown, namely the homologous complex of the anti-POD with the rat antibodies and the homologous complex of the anti-AP with the rat antibodies. This shows that no bifunctional complex is formed when two homologous complexes are mixed with each other.

EXAMPLE II

PREPARATION OF HOMOLOGOUS CYCLIC TETRAMERIC COMPLEX OF ANTI-IMMUNOGLOBULIN.

To 100 μl of a solution of monoclonal antibodies having specificity for human IgG of the mouse IgG1-class in a concentration of 1 mg/ml in phosphate buffered saline having a pH of 7.2 with 0.1% (weight/volume) NaN$_3$ is added 100 μl of rat-anti-mouse antibody (see example Ic) having a concentration of 1 mg/ml. The latter solution also contains 0.1% (weight/volume) NaN$_3$.

This mixture can be used in a dilution of 1:1000 as Coombs reagent in an indirect agglutination technique to detect binding of Rhesus antibodies to human blood cells.

EXAMPLE III

PREPARATION OF A LABELLED BIFUNCTIONAL COMPLEX.

To 100 µl of a solution of monoclonal mouse antibodies anti-leu-3a (Becton and Dickinson, commercially available) having a concentration of 0.1 mg/ml in PBS (pH 7.2) with 0.2% (weight/volume) gelatine and 0.1% (weight/volume) NaN$_3$ there are added 200 µl of a solution of monoclonal mouse-anti-alkaline phosphatase antibodies (see example Ib) having a concentration of 0.2 mg/ml. Then 100 µl of a solution of rat-anti-mouse antibodies (see Example Ic) having a concentration of 1 mg/ml and finally 200 µl of a solution of alkaline phosphatase (Sigma, Grade VII) having a concentration of 2.5 mg/ml in PBS (pH 7.2) are added to the mixture of mouse IgG1 antibodies.

This mixture can be used in a dilution of 50 to 100 times for detection of leu-3a positive cells in cryostate sections of, for example, human skin.

EXAMPLE IV

Monoclonal mouse IgG1-anti-erythrocyte antibodies and mouse IgG1-anti-HLA-DR antibodies were mixed in a molar ratio of 1:4. Then the monoclonal rat-anti-mouse antibodies (see example Ic) were added in an amount equivalent to the total of the mouse antibodies. The mixture was used for labelling erythrocytes. For that purpose the above-mentioned mixture of antibodies was added in such an amount to an erythrocyte suspension having a concentration of 10$^8$ cells/ml that the final concentration calculated on the mouse-antibodies used was 50 µg/ml. Then there was incubated during 60 minutes at 0° C. Subsequently the labelled erythrocytes were washed with PBS-BSA, the mixture was centrifuged (200 g; 10 min.) and was again suspended in the original volume of PBS-BSA. Then human mononuclear peripheral blood cells were added in a ratio of erythrocytes to human mononuclear peripheral blood cells of 10:1. After centrifuging (200 g; 10 min.) there was incubated during 60 minutes at 0° C. Then the sediment was carefully suspended in PBS-BSA. Cytocentrifuge preparations of the suspension were stained with May-Grünwald Giemsa. Clear rosettes appeared to have been formed, which consist of erythrocyte coated HLA-DR-positive cells. The percentage of rosette forming, nucleus containing cells (25%) agrees well with the percentage of HLA-DR-positive cells (29%) which is determined by means of a step-wise amplified immuno-peroxidase staining (J. Histochemistry and Cytochemistry 32, Nr. 2, pages 172-178 (1984)). When the same test is carried out, but the anti-HLA-DR antibodies are replaced with anti-peroxidase antibodies, no rosettes are formed.

I claim:

1. A immunological bifunctional complex of two different antibodies of a first animal species which have been conjugated to form a cyclic tetramer with two monoclonal antibodies of a second animal species directed against the Fc-fragment of the antibodies of the first animal species.

2. Immunological bifunctional complex according to claim 1 coupled with the antigen against which one of the antibodies of the first animal species is directed.

3. The immunological bifunctional complex according to claim 1, characterized in that the Fab-fragments of one of the antibodies of the first animal species are directed against a detectible substance or a substance having toxic or therapeutic activity.

4. Immunological complex according to claim 3, characterized in that the substance is a detectable substance.

5. Immunological complex according to claim 4, characterized in that the detectable substance is an enzyme.

6. Immunological complex according to claim 5, characterized in that the enzyme is peroxidase.

7. Immunological complex according to claim 1, characterized in that the Fab-fragments of one of the antibodies of the first animal species are directed against a detectable substance, and the Fab-fragments of the other antibody of the first animal species are directed against an antigen to be assayed in an immunoassay, surface membrane antigens, a viral antigen or an antigen produced by a malignant cell.

8. Immunological complex according to claim 7, characterized in that the antigen is a plasma protein.

9. Immunological complex according to claim 7, characterized in that the antigen is a protein present on the surface of a particle.

10. Immunological complex according to claim 9, characterized in that the protein in a protein present on the surface of blood cells.

11. Immunological complex according to claim 10, characterized in that the blood cells are erythrocytes or blood platelets.

12. Immunological complex according to claim 1, characterized in that the first animal species is the mouse and the second animal species is the rat.

13. A process for carrying out immunological reactions, characterized in that a bifunctional immunological complex as in any one of claims 1 and 2-12 is used therein.

14. The immunological complex as in any of claims 7-11, characterized in that the detectable substance is an enzyme.

15. The immunological complex as in any of claims 7-12, characterized in that the detectable substance is peroxidase.

16. The immunological complex according to claim 1, characterized in that the Fab-fragments of one of the antibodies of the first animal species are directed against a substance having toxic or therapeutic activity and the Fab-fragments of the other antibody of the first animal species are directed against a surface-membrane antigen.

17. The immunological complex according to claim 16, characterized in that the Fab fragments directed against a substance having toxic or therapeutic activity are coupled with the substance having toxic or therapeutic activity.

18. The immunological complex according to claim 1, characterized in that the Fab fragments of one of the antibodies of the first animal species are directed against an effector cell, and the Fab-fragments of the other antibody of the first animal species are directed against a surface-membrane antigen.

19. The immunological complex according to claim 16, 17 or 18, characterized in that the surface-membrane antigen is an antigen on the surface of a tumor cell, a virus infected cell or a microorganism.

20. A process for preparing bifunctional immunological complexes, characterized in that two different antibodies of a first animal species are reacted with an about equimolar amount of antibodies of a second animal species which are directed against the Fc-fragments of the antibodies of the first animal species, and that the tetrameric complex formed is isolated.

21. The process of claim 20, characterized in that the bifunctional complexes formed are reacted with an antigen against which one of the antibodies of the first animal species is directed.

22. The process as in any one of claims 20–24, characterized in that the tetrameric complex is isolated by means of anion-exchange chromatography.

23. The process of claim 21, charactertized in that the Fab-fragments of one of the antibodies of the first animal species are directed against a detectable substance or a substance having toxic or therapeutic activity.

24. The process of claim 23, characterized in that the substance is a detectable substance.

25. The process of claim 24, characterized in that the substance is an enzyme.

26. The process of claim 25, characterized in that the enzyme is peroxidase.

27. The process of claim 21, characterized in that the Fab-fragments of one of the antibodies of the first animal species are directed against a detectable substance and the Fab-fragments of the other antibody of the first animal species are directed against an antigen to be assayed in an immunoassay, surface membrane antigens, or an antigen produced by a malignant cell.

28. The process of claim 27, characterized in that the antigen is a plasma protein.

29. The process of claim 27, characterized in that the antigen is a protein present on the surface of a particle.

30. The process of claim 29, characterized in that the protein is a protein present on the surface of blood cells.

31. The process of claim 30, characterized in that the blood cells are erythrocytes or blood platelets.

32. The process of claim 21, characterized in that the first animal species is the mouse and the second animal species is the rat.

33. The process as in any one of claims 27 to 32 characterized in that the detectable substance is an enzyme.

34. The process as in any one of claims 27 to 32 characterized in that the detectable substance is peroxidase.

* * * * *